United States Patent [19]
Malle et al.

[11] Patent Number: 6,118,008
[45] Date of Patent: Sep. 12, 2000

[54] DIAMINO PYRAZOLS, THEIR SYNTHESIS, KERATIN FIBRE DYEING COMPOSITIONS CONTAINING THEM, KERATIN FIBRE DYEING METHODS

[75] Inventors: Gérard Malle, Villiers sur Morin; Laurent Vidal, Paris; Agnès Burande, Villeparisis; Mireille Maubru, Chatou, all of France

[73] Assignee: L'Oreal, Paris, France

[21] Appl. No.: 09/180,183

[22] PCT Filed: Apr. 25, 1997

[86] PCT No.: PCT/FR97/00750

§ 371 Date: May 7, 1999

§ 102(e) Date: May 7, 1999

[87] PCT Pub. No.: WO97/42173

PCT Pub. Date: Nov. 13, 1997

[30] Foreign Application Priority Data

May 3, 1996 [FR] France .................................. 96 05579

[51] Int. Cl.$^7$ ............................ C07D 231/38; A61K 7/13
[52] U.S. Cl. ........................ 548/371.4; 8/423; 548/372.1
[58] Field of Search ............................. 548/371.4, 372.1; 8/423

[56] References Cited

U.S. PATENT DOCUMENTS 5,500,439  3/1996  Ulrich et al. ........................ 548/371.4

FOREIGN PATENT DOCUMENTS

| 0 375 977 | 7/1990 | European Pat. Off. . |
| 2 586 913 | 3/1987 | France . |
| 2 630 438 | 10/1989 | France . |
| 4 234 885 | 4/1994 | Germany . |
| 4 234 886 | 4/1994 | Germany . |
| 4 234 887 | 4/1994 | Germany . |

OTHER PUBLICATIONS

English Language Derwent Abstract of DE 4 234 885. (1994).
English Language Derwent Abstract of FR 2 586 913. (1987).
English Language Derwent Abstract of FR 2 630 438. (1989).

*Primary Examiner*—Robert W. Ramsuer
*Attorney, Agent, or Firm*—Finnegan, Henderson, Farabow, Garrett & Dunner L.L.P.

[57] ABSTRACT

The invention discloses new 5-substituted 3,4-diamino pyrazols, their methods of preparation, compositions for keratin fiber oxidation dyeing containing them as an oxidizing base, and the dyeing methods using same.

27 Claims, No Drawings

DIAMINO PYRAZOLS, THEIR SYNTHESIS, KERATIN FIBRE DYEING COMPOSITIONS CONTAINING THEM, KERATIN FIBRE DYEING METHODS

This application is a 371 of PCT/FR 97/100750 filed Apr. 25, 1997.

The subject-matter of the invention is novel 5-substituted 3,4-diaminopyrazole compounds, their processes of preparation, the compositions for the oxidation dyeing of keratinous fibres comprising them as oxidation base, and dyeing methods employing this composition.

It is known to dye keratinous fibres, and in particular human hair, with dyeing compositions comprising oxidation dye precursors, in particular ortho- or para-phenylenediamines, ortho- or para-aminophenols, or heterocyclic compounds, such as diaminopyrazole derivatives, generally known as oxidation bases. Oxidation dye precursors, or oxidation bases, are colourless or weakly coloured compounds which, in combination with oxidants, can give rise, by an oxidative coupling process, to coloured and colouring compounds.

It is also known that it is possible to vary the shades obtained with these oxidation bases by combining them with couplers or colouring modifiers, the latter being chosen in particular from aromatic meta-diamines, meta-aminophenols, meta-diphenols and certain heterocyclic compounds.

The variety of molecules employed as oxidation bases and couplers makes it possible to obtain a rich palette of colours.

The so-called "permanent" colouring obtained by virtue of these oxidation dyes must, furthermore, satisfy a certain number of requirements. Thus, it must be without disadvantage toxicologically, it must make it possible to obtain shades in the desired intensity and it must behave well in the face of external agents (light, weathering, washing, permanent waving, perspiration or rubbing).

The dyes must also make it possible to cover white hair and, finally, must be as non-selective as possible, that is to say must make it possible to obtain differences in colouring which are as slight as possible all along the same keratinous fibre, because the fibre can exhibit different sensitivity (i.e. damage) between its tip and its root.

para-Aminophenol is generally used, alone or as a mixture with other bases and in combination with appropriate couplers, to obtain red shades and para-phenylenediamines are generally used to obtain blue shades.

Provision has already been made, in particular in Patent Application EP-A-375,977, to use certain diaminopyrazole derivatives, namely, more specifically, 3,4-diaminopyrazole compounds, for the oxidation dyeing of keratinous fibres in red shades. However, the use of the diaminopyrazoles disclosed in this patent application does not make it possible to obtain a rich palette of colours and, furthermore, the method for preparing these compounds is lengthy and expensive.

The Applicant Company has now just discovered, entirely unexpectedly and surprisingly, that novel 5-substituted 3,4-diaminopyrazole compounds of formula (I) defined below are not only suitable for use as oxidation dye precursors but, in addition, they make it possible to obtain dyeing compositions resulting in shades with highlights ranging from red to blue and also, surprisingly, in natural shades. These compounds turn out to be easy to synthesize.

The Applicant Company has also discovered, unexpectedly, that, with these novel 5-substituted 3,4-diaminopyrazole compounds of formula (I) defined below, the colorations obtained at acidic pH were more intense than those obtained at basic pH.

Finally, it has been discovered that the 5-substituted 3,4-diaminopyrazoles of the invention resulted in a better absorption of dye on locks and in colorations which are more resistant to light than those obtained with the 3,4-diaminopyrazole compounds unsubstituted at the 5 position known in the prior art, in particular those disclosed in Application EP-A-375,977.

These discoveries are at the basis of the present invention.

A first subject-matter of the invention is thus novel 5-substituted 3,4-diaminopyrazole compounds of the following formula (I) and their addition salts with an acid:

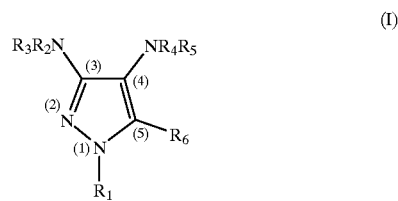

in which:

$R_1$, $R_2$, $R_3$, $R_4$ and $R_5$, which are identical or different, represent a hydrogen atom; a linear or branched $C_1$–$C_6$ alkyl radical; a $C_2$–$C_4$ hydroxyalkyl radical; a $C_2$–$C$ aminoalkyl radical; a phenyl radical; a phenyl radical substituted by a halogen atom or a $C_1$–$C_4$ alkyl, $C_1$–$C_4$ alkoxy, nitro, trifluoromethyl, amino or $C_4$–$C_4$ alkylamino radical; a benzyl radical; or a benzyl radical substituted by a halogen atom or by a $C_1$–$C_4$ alkyl, $C_1$–$C_4$ alkoxy, methylenedioxy, hydroxyl, $C_1$–$C_4$ hydroxyalkyl, amino or $C_1$–$C_4$ alkylamino radical; at most one of the $R_2$ to $R_5$ radicals can denote a radical

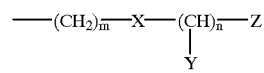

in which m and n are integers, which are identical or different, of between 1 and 3 inclusive, X represents an oxygen atom or an NH group, Y represents a hydrogen atom or else a methyl radical, and Z represents a methyl radical or an OR or NRR' group in which R and R', which can be identical or different, denote a hydrogen atom, a methyl radical or an ethyl radical; it being understood that, when $R_2$ represents a hydrogen atom, then $R_3$ can represent an amino or $C_1$–$C_4$ alkylamino radical;

$R_6$ represents a linear or branched $C_1$–$C_6$ alkyl radical; a $C_1$–$C_4$ hydroxyalkyl radical; a $C_1$–$C_4$ aminoalkyl radical; a phenyl radical; a phenyl radical substituted by a halogen atom or by a $C_1$–$C_4$ alkyl, $C_1$–$C_4$ alkoxy, nitro, trifluoromethyl, amino or $C_1$–$C_4$ alkylamino radical; a benzyl radical; a benzyl radical substituted by a halogen atom or by a $C_1$–$C_4$ alkyl, $C_1$–$C_4$ alkoxy, nitro, trifluoromethyl, amino or $C_1$–$C_4$ alkylamino radical; a heterocycle chosen from thiophene, furan and pyridine; or a —$(CH_2)_p$—O—$(CH_2)_q$—OR" radical, in which p and q are integers, which are identical or different, of between 1 and 3 inclusive and R" represents a hydrogen atom or a methyl radical; it being understood that, in the above formula (I):

at least one of the $R_4$ and $R_5$ radicals represents a hydrogen atom, when that $R_2$, respectively $R_4$, represents a substituted or unsubstituted phenyl radical or a benzyl radical or a radical

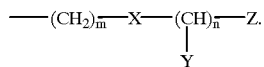

then $R_3$, respectively $R_5$, cannot represent any of these three radicals, $R_1$ can also represent a heterocyclic residue of the following types: 2-, 3- or 4-pyridyl, 2- or 3-thienyl, or 2- or 3-furyl, optionally substituted by a methyl radical.

Generally, the addition salts with an acid which can be used in the context of the dyeing compositions of the invention (oxidation bases and couplers) are chosen in particular from hydrochlorides, hydrobromides and sulphates and tartrates, lactates and acetates.

Mention may in particular be made, among the 5-substituted 3,4-diaminopyrazoles of formula (I) of the invention, of:

3,4-diamino-5-ethylpyrazole;
3,4-diamino-5-methylpyrazole;
3,4-diamino-5-isopropylpyrazole;
3,4-diamino-5-tert-butylpyrazole;
3,4-diamino-5-phenylpyrazole;
3,4-diamino-5-methoxypyrazole;
3,4-diamino-5-(4'-methoxyphenyl)pyrazole;
3,4-diamino-5-(3'-methoxyphenyl)pyrazole;
3,4-diamino-5-(2'-methoxyphenyl)pyrazole;
3,4-diamino-5-(4'-methylphenyl)pyrazole;
3,4-diamino-5-(3'-methylphenyl)pyrazole;
3,4-diamino-5-(2'-chlorophenyl)pyrazole;
3,4-diamino-5-(4'-chlorophenyl)pyrazole;
3,4-diamino-5-(3'-trifluoromethylphenyl)pyrazole;
3,4-diamino-1,5-dimethylpyrazole;
3,4-diamino-5-ethyl-1-methylpyrazole;
3,4-diamino-1-methyl-5-tert-butylpyrazole;
3,4-diamino-1-methyl-5-phenylpyrazole;
3,4-diamino-1-methyl-5-methoxypyrazole;
3,4-diamino-1-methyl-5-(4'-methoxyphenyl)pyrazole;
3,4-diamino-1-methyl-5-(3'-methoxyphenyl)pyrazole;
3,4-diamino-1-methyl-5-(2'-methoxyphenyl)pyrazole;
3,4-diamino-1-methyl-5-(4'-methylphenyl)pyrazole;
3,4-diamino-1-methyl-5-(3'-methylphenyl)pyrazole;
3,4-diamino-5-(2'-chlorophenyl)-1-methylpyrazole;
3,4-diamino-5-(4'-chlorophenyl)-1-methylpyrazole;
3,4-diamino-5-(3'-trifluoromethylphenyl)-1-methylpyrazole;
3,4-diamino-1-ethyl-5-methylpyrazole;
3,4-diamino-1,5-diethylpyrazole;
3,4-diamino-1-ethyl-5-tert-butylpyrazole;
3,4-diamino-1-ethyl-5-phenylpyrazole;
3,4-diamino-1-ethyl-5-methoxypyrazole;
3,4-diamino-1-ethyl-5-(4'-methoxyphenyl)pyrazole;
3,4-diamino-1-ethyl-5-(3'-methoxyphenyl)pyrazole;
3,4-diamino-1-ethyl-5-(2'-methoxyphenyl)pyrazole;
3,4-diamino-1-ethyl-5-(4'-methylphenyl)pyrazole;
3,4-diamino-1-ethyl-5-(3'-methylphenyl)pyrazole;
3,4-diamino-5-(2'-chlorophenyl)-1-ethylpyrazole;
3,4-diamino-5-(4'-chlorophenyl)-1-ethylpyrazole;
3,4-diamino-1-ethyl-5-(3'-trifluoromethylphenyl)pyrazole;
3,4-diamino-1-isopropyl-5-methylpyrazole;
3,4-diamino-5-ethyl-1-isopropylpyrazole;
3,4-diamino-1-isopropyl-5-tert-butylpyrazole;
3,4-diamino-1-isopropyl-5-phenylpyrazole;
3,4-diamino-1-isopropyl-5-methoxypyrazole;
3,4-diamino-1-isopropyl-5-(4'-methoxyphenyl)pyrazole;
3,4-diamino-1-isopropyl-5-(3'-methoxyphenyl)pyrazole;
3,4-diamino-1-isopropyl-5-(2'-methoxyphenyl)pyrazole;
3,4-diamino-1-isopropyl-5-(4'-methylphenyl)pyrazole;
3,4-diamino-1-isopropyl-5-(3'-methylphenyl)pyrazole;
3,4-diamino-5-(2'-chlorophenyl)-1-isopropylpyrazole;
3,4-diamino-5-(4'-chlorophenyl)-1-isopropylpyrazole;
3,4-diamino-1-isopropyl-5-(3'-trifluoromethylphenyl)pyrazole;
3,4-diamino-5-methyl-1-propylpyrazole;
3,4-diamino-5-ethyl-1-propylpyrazole;
3,4-diamino-1-propyl-5-tert-butylpyrazole;
3,4-diamino-5-phenyl-1-propylpyrazole;
3,4-diamino-5-methoxy-1-propylpyrazole;
3,4-diamino-5-(4'-methoxyphenyl)-1-propylpyrazole;
3,4-diamino-5-(3'-methoxyphenyl)-1-propylpyrazole;
3,4-diamino-5-(2'-methoxyphenyl)-1-propylpyrazole;
3,4-diamino-5-(4'-methylphenyl)-1-propylpyrazole;
3,4-diamino-5-(3'-methylphenyl)-1-propylpyrazole;
3,4-diamino-5-(2'-chlorophenyl)-1-propylpyrazole;
3,4-diamino-5-(4'-chlorophenyl)-1-propylpyrazole;
3,4-diamino-1-propyl-5-(3'-trifluoromethylphenyl)pyrazole;
1-benzyl-3,4-diamino-5-methylpyrazole;
1-benzyl-3,4-diamino-5-ethylpyrazole;
1-benzyl-3,4-diamino-5-tert-butylpyrazole;
1-benzyl-3,4-diamino-5-phenylpyrazole;
1-benzyl-3,4-diamino-5-methoxypyrazole;
1-benzyl-3,4-diamino-5-(4'-methoxyphenyl)pyrazole;
1-benzyl-3,4-diamino-5-(3'-methoxyphenyl)pyrazole;
1-benzyl-3,4-diamino-5-(2'-methoxyphenyl)pyrazole;
1-benzyl-3,4-diamino-5-(4'-methylphenyl)pyrazole;
1-benzyl-3,4-diamino-5-(3'-methylphenyl)pyrazole;
1-benzyl-3,4-diamino-5-(2'-chlorophenyl)pyrazole;
1-benzyl-3,4-diamino-5-(4'-chlorophenyl)pyrazole;
1-benzyl-3,4-diamino-5-(3'-trifluoromethylphenyl)pyrazole;
1-[4'-chlorobenzyl]-3,4-diamino-5-methylpyrazole;
1-[4'-chlorobenzyl]-3,4-diamino-5-ethylpyrazole;
1-[4'-chlorobenzyl]-3,4-diamino-5-tert-butylpyrazole;
1-[4'-chlorobenzyl]-3,4-diamino-5-phenylpyrazole;
1-[4'-chlorobenzyl]-3,4-diamino-5-methoxypyrazole;
1-[4'-chlorobenzyl]-3,4-diamino-5-(4'-methoxyphenyl)pyrazole;
1-[4'-chlorobenzyl]-3,4-diamino-5-(3'-methoxyphenyl)pyrazole;
1-[4'-chlorobenzyl]-3,4-diamino-5-(2'-methoxyphenyl)pyrazole;
1-[4'-chlorobenzyl]-3,4-diamino-5-(4'-methylphenyl)pyrazole;
1-[4'-chlorobenzyl]-3,4-diamino-5-(3'-methylphenyl)pyrazole;
1-[4'-chlorobenzyl]-3,4-diamino-5-(2'-chlorophenyl)pyrazole;
1-[4'-chlorobenzyl]-3,4-diamino-5-(4'-chlorophenyl)pyrazole;
1-[4'-chlorobenzyl]-3,4-diamino-5-(3'-trifluoromethylphenyl)pyrazole;
3,4-diamino-5-hydroxymethyl-1-methylpyrazole;
3,4-diamino-5-hydroxymethyl-1-ethylpyrazole;
3,4-diamino-5-hydroxymethyl-1-isopropylpyrazole;
3,4-diamino-5-hydroxymethyl-1-propylpyrazole;
1-benzyl-3,4-diamino-5-hydroxymethylpyrazole;
1-[4'-chlorobenzyl]-3,4'-diamino-5-hydroxymethylpyrazole;
5-aminomethyl-3,4-diamino-1-methylpyrazole;
5-aminomethyl-3,4-diamino-1-ethylpyrazole;
5-aminomethyl-3,4-diamino-1-isopropylpyrazole;

5-aminomethyl-3,4-diamino-1-propylpyrazole;
5-aminomethyl-1-benzyl-3,4-diaminopyrazole;
5-aminomethyl-1-[4'-chlorobenzyl]-3,4-diaminopyrazole;
3,4-diamino-5-hydroxymethylpyrazole;
3,4-diamino-5-[β-hydroxyethylamino]-1-methylpyrazole;
3,4-diamino-5-[β-hydroxyethylamino]-1-ethylpyrazole;
3,4-diamino-5-[β-hydroxyethylamino]-1-isopropylpyrazole;
3,4-diamino-5-[β-hydroxyethylamino]-1-propylpyrazole;
3,4-diamino-5-[β-hydroxyethylamino]pyrazole;
1-benzyl-3,4-diamino-5-[β-hydroxyethylamino]pyrazole;
1-[4'-chlorobenzyl]-3,4-diamino-5-[β-hydroxyethylamino]pyrazole;

and their addition salts with an acid.

Preference is more particularly given, among these 5-substituted 3,4-diaminopyrazoles, to:

3,4-diamino-5-methylpyrazole;
3,4-diamino-5-ethylpyrazole;
3,4-diamino-5-isopropylpyrazole;
3,4-diamino-5-tert-butylpyrazole;
3,4-diamino-5-phenylpyrazole;
3,4-diamino-5-(4'-methoxyphenyl)pyrazole;
3,4-diamino-5-(3'-methoxyphenyl)pyrazole;
3,4-diamino-5-(2'-methoxyphenyl)pyrazole;
3,4-diamino-5-(4'-methylphenyl)pyrazole;
3,4-diamino-5-(3'-methylphenyl)pyrazole;
5-(2'-chlorophenyl)-3,4-diaminopyrazole;
5-(4'-chlorophenyl)-3,4-diaminopyrazole;
3,4-diamino-1,5-dimethylpyrazole;
3,4-diamino-5-ethyl-1-methylpyrazole;
3,4-diamino-5-isopropyl-1-methylpyrazole;
3,4-diamino-1-methyl-5-tert-butylpyrazole;
3,4-diamino-1-methyl-5-phenylpyrazole;
3,4-diamino-1-methyl-5-methoxypyrazole;
3,4-diamino-1-methyl-5-(4'-methoxyphenyl)pyrazole;
3,4-diamino-1-methyl-5-(3'-methoxyphenyl)pyrazole;
3,4-diamino-1-methyl-5-(2'-methoxyphenyl)pyrazole;
3,4-diamino-1-methyl-5-(4'-methylphenyl)pyrazole;
3,4-diamino-1-methyl-5-(3'-methylphenyl)pyrazole;
5-(2'-chlorophenyl)-3,4-diamino-1-methylpyrazole;
5-(4'-chlorophenyl)-3,4-diamino-1-methylpyrazole;

and their addition salts with an acid.

Another subject-matter of the invention is the methods for preparing the novel compounds of formula (I).

When $R_1$ represents a hydrogen atom (compounds of formula (IA) below), use is preferably made of Method A, corresponding to the following synthetic scheme:

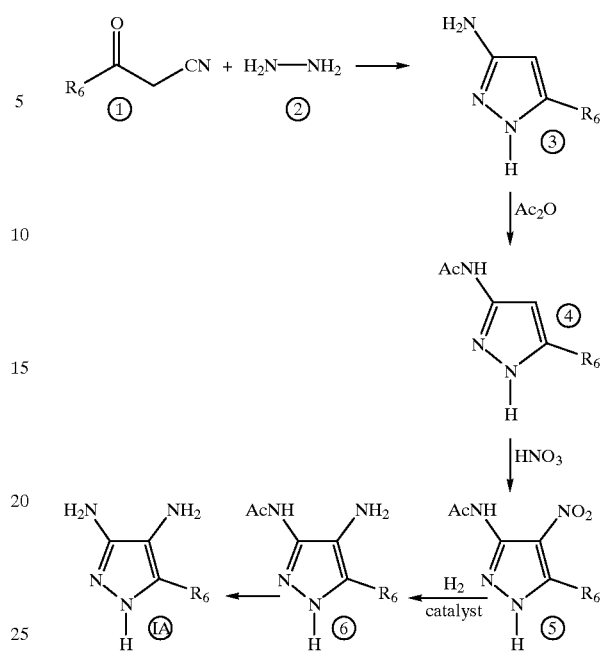

METHOD A which consists in reacting, in a first stage, a β-ketonitrile 1 with hydrazine 2, at a temperature generally greater than 90° C. and preferably of between 95 and 150° C., in an alcoholic solvent, in order to obtain the 3-aminopyrazole 3. The 3-aminopyrazole 3 is subsequently acetylated at the 3 position in order to result in the 3-acetamidopyrazole 4, which is itself nitrated at the 4 position and then hydrogenated and deacetylated, in order to give the 3,4-diamiinopyrazole of formula (IA). The nitration of 4 is carried out with fuming nitric acid in concentrated sulphuric medium at a temperature of between 0 and 5° C.

For good control of the temperature during the first stage, it is preferable generally to operate at reflux of the solvent used. Mention may more particularly be made, among the alcohols used as reaction solvent, of n-propanol, 1-butanol, 2-butanol, 2-methyl-1-butanol, 3-methyl-1-butanol, 2-methyl-1-propanol, n-pentanol, 2-pentanol, 3-methyl-3-pentanol, 4-methyl-2-pentanol or 2-ethyl-1-butanol.

The catalytic hydrogenation of the compound 5 is preferably carried out in a lower alcohol in the presence of a catalyst, such as palladium-on-charcoal, at a temperature generally of between 20 and 100° C. Finally, the deacetylation of the compound 6 is preferably carried out in hydrochloric acid at a temperature generally of between 40 and 100° C.

When $R_2$ is other than a hydrogen atom (compounds of formula (IB) below), use is preferably made of Method B, corresponding to the following synthetic scheme:

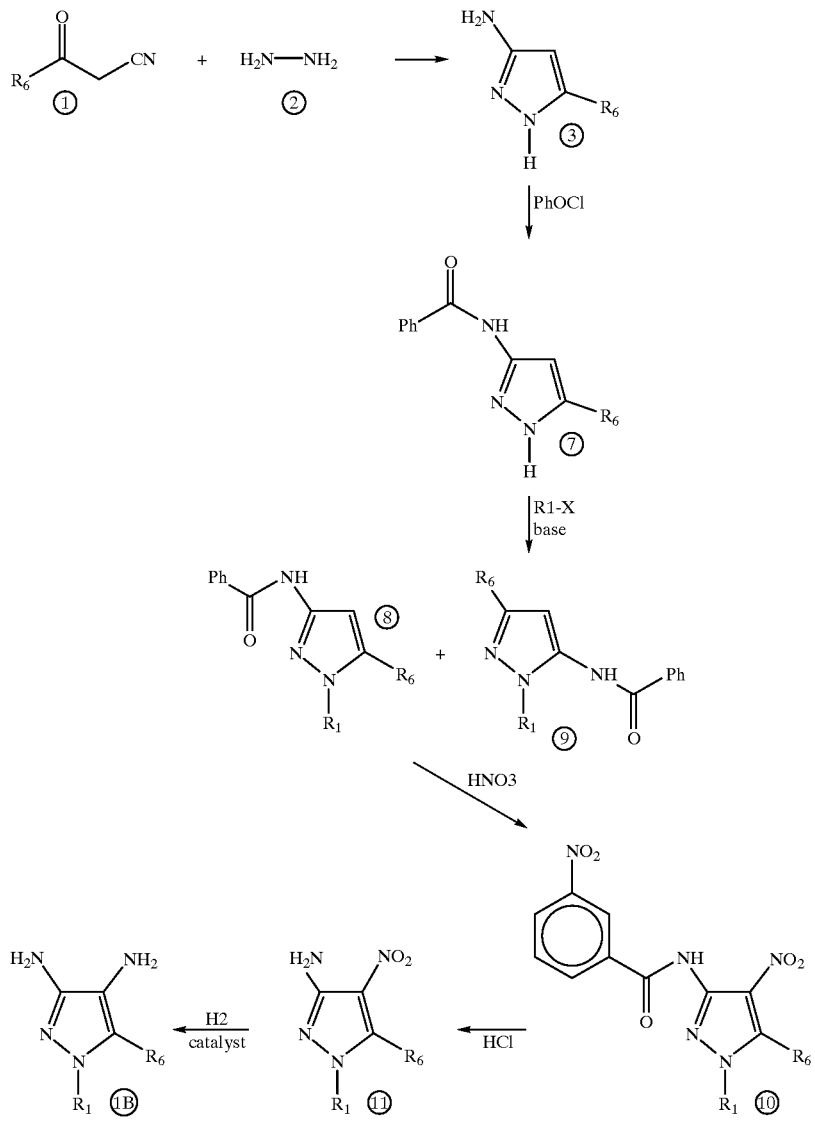

METHOD B which consists in reacting, in a first stage, a β-ketonitrile 1 with hydrazine 2 according to the operating conditions mentioned for Method A described above, in order to obtain the 3-aminopyrazole 3, which, in a second stage, is benzoylated in the presence of benzoic acid chloride in an aprotic solvent, at a temperature generally of between 5 and 60° C. and in the presence of a base, in order to result in the compound 7.

It is preferable generally to operate in a solvent such as linear, branched or cyclic lower ethers and in particular diethyl ether, diisopropyl ether, tetrahydrofuran or dioxane. Halogenated solvents are also used and it is preferable to operate in dichloromethane, chloroform or tetrachloroethane.

The bases employed are generally, and preferably, carbonate or hydrogencarbonate salts, such as those of lithium, sodium or potassium, or else organic bases of the family of aliphatic or aromatic amines, such as triethylamine, N-methylmorpholine, morpholine, methyldiethylamine, pyridine or 4-dimethylaminopyridine.

In a third stage, the compound 7 is reacted with an aliphatic halide of the chloro-, bromo- or iodoalkyl class at a temperature generally of between 10 and 100° C. in an aprotic solvent of the class of linear or branched aliphatic ethers, in order to result in a mixture of 5-benzoylaminopyrazole 9 and of 3-benzoylaminopyrazole 8. The separation of the two regioisomers 8 and 9 is preferably carried out by silica gel chromatography or by recrystallization, optionally fractional recrystallization.

In a fourth stage, the compound 8 is nitrated with fuming nitric acid in concentrated sulphuric medium at a temperature of between 0 and 5° C., in order to result in the compound 10.

In a fifth stage, the compound 10 is debenzoylated in the presence of concentrated hydrochloric acid at a temperature preferably of between 40 and 100° C., in order to result in the 3-amino-4-nitropyrazole 11.

In a sixth stage, the compound 11 is reduced by catalytic hydrogenation in a lower alcohol in the presence of a catalyst, such as palladium-on-charcoal, at a temperature preferably of between 20 and 100° C., in order to result in the 3,4-diaminopyrazole of formula (IB).

Another subject-matter of the invention is a composition for the oxidation dyeing of keratinous fibres and in particular human keratinous fibres, such as hair, characterized in that it comprises, in a medium appropriate for dyeing, at least one 5-substituted 3,4-diaminopyrazole of formula (I) as defined above as oxidation base and/or at least one of its addition salts with an acid.

The 5-substituted 3,4-diaminopyrazole(s) of formula (I) above and their acid addition salts preferably represent from 0.0005 to 12% by weight approximately of the total weight of the dyeing composition and more preferably still from 0.005 to 6% by weight approximately of this weight.

The medium appropriate for the dyeing (or vehicle) is generally composed of water or of a mixture of water and of at least one organic solvent for dissolving the compounds which would not be sufficiently soluble in water. Mention may be made, as organic solvent, of, for example, lower $C_1-C_4$ alkanols, such as ethanol and isopropanol; glycerol; glycols and glycol ethers, such as 2-butoxyethanol, propylene glycol, propylene glycol monomethyl ether, or diethylene glycol monoethyl ether and monomethyl ether; and aromatic alcohols, such as benzyl alcohol or phenoxyethanol, the analogous products and their mixtures.

The solvents can be present in proportions preferably of between 1 and 40% by weight approximately with respect to the total weight of the dyeing composition and more preferably still between 5 and 30% by weight approximately.

The pH of the dyeing composition in accordance with the invention is generally between 3 and 12 approximately and preferably between 5 and 11 approximately. It can be adjusted to the desired value by means of acidifying or basifying agents commonly used in dyeing keratinous fibres.

Mention may be made, among acidifying agents, by way of example, of inorganic or organic acids, such as hydrochloric acid, orthophosphoric acid, sulphuric acid, carboxylic acids, such as acetic acid, tartaric acid, citric acid or lactic acid, or sulphonic acids.

Mention may be made, among basifying agents, by way of example, of ammonia, alkaline carbonates, alkanolamines, such as mono-, di- and triethanolamines and their derivatives, sodium hydroxide, potassium hydroxide and the compounds of following formula (II):

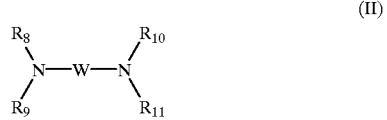

(II)

in which W is a propylene residue optionally substituted by a hydroxyl group or a $C_1-C_4$ alkyl radical and $R_8$, $R_9$, $R_{10}$ and $R_{11}$, which are identical or different, represent a hydrogen atom or a $C_1-C_4$ alkyl or $C_1-C_4$ hydroxyalkyl radical.

The dyeing composition in accordance with the invention can also comprise, in addition to the dyes defined above, at least one additional oxidation base, other than the 5-substituted 3,4-diaminopyrazoles used in accordance with the invention, which can be chosen from oxidation bases conventionally used in oxidation dyeing and among which may in particular be mentioned para-phenylenediamines, bisphenylalkylenediamines, para-aminophenols, ortho-aminophenols and heterocyclic bases.

Mention may more particularly be made, among para-phenylenediamines, by way of example, of para-phenylenediamine, para-toluylenediamine, 2,6-dimethyl-para-phenylenediamine, 2-(β-hydroxyethyl)-para-phenylenediamine, 2-n-propyl-para-phenylenediamine, 2-isopropyl-para-phenylenediamine, N-(β-hydroxypropyl)-para-phenylenediamine, N,N-bis(β-hydroxyethyl)-para-phenylenediamine, 4-amino-N-(β-methoxyethyl)aniline, the para-phenylenediamines disclosed in French Patent Application FR-A-2,630,438, and their addition salts with an acid.

Mention may more particularly be made, among bisphenylalkylenediamines, by way of example, of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-amino-phenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and their addition salts with an acid.

Mention may more particularly be made, among para-aminophenols, by way of example, of para-aminophenol, 4-amino-3-methylphenol, 4-amino-3-fluorophenol, 4-amino-3-(hydroxymethyl)phenol, 4-amino-2-methylphenol, 4-amino-2-(hydroxymethyl)phenol, 4-amino-2-(methoxyethyl)phenol, 4-amino-2-(aminomethyl)phenol, 4-amino-2-[(β-hydroxyethyl)aminomethyl]phenol and their addition salts with an acid.

Mention may more particularly be made, among ortho-aminophenols, by way of example, of 2-aminophenol, 2-amino-5-methylphenol, 2-amino-6-methylphenol, 5-acetamido-2-aminophenol and their addition salts with an acid.

Mention may more particularly be made, among heterocyclic bases, by way of example, of pyridine derivatives, pyrimidine derivatives or pyrazole derivatives.

When they are used, these additional oxidation bases preferably represent from 0.0005 to 12% by weight approximately of the total weight of the dyeing composition and more preferably still from 0.005 to 6% by weight approximately of this weight.

The oxidation dyeing compositions in accordance with the invention can also include at least one coupler and/or at least one direct dye, in particular for modifying the shades or enriching them with highlights.

The couplers which can be used in the oxidation dyeing compositions according to the invention can be chosen from the couplers conventionally used in oxidation dyeing and among which may in particular be mentioned meta-phenylenediamines, meta-aminophenols, meta-diphenols, heterocyclic couplers, such as, for example, indole derivatives, indoline derivatives, pyridine derivatives and pyrazolones, naphthalene derivatives, such as monohydroxynaphthalenes and dihydroxynaphthalenes, and their addition salts with an acid.

These couplers are more particularly chosen from 1,3-diaminobenzene, 2,4-diamino-1-(β-hydroxyethyloxy)benzene, 1-methoxy-2-amino-4-[(β-hydroxyethyl)amino]benzene, 4,6-bis(2-hydroxyethoxy)-1,3-diaminobenzene, 3-aminophenol, 1-methyl-2-hydroxy-4-aminobenzene, 1-methyl-2-hydroxy-4-[(2-hydroxyethyl)amino]benzene, 1,3-dihydroxybenzene, 1,3-dihydroxy-4-chlorobenzene, 1,3-dihydroxy-2-methylbenzene, 6-hydroxybenzomorpholine, 1-(β-hydroxyethyl)amino-3,4-(methylenedioxy)benzene, 6-hydroxyindole, 1,2-methylenedioxy-β-methoxy-4-aminobenzene, 4-hydroxybenzimidazole and their addition salts with an acid.

When they are present, these couplers preferably represent from 0.0001 to 10% by weight approximately of the total weight of the dyeing composition and more preferably still from 0.005 to 5% by weight approximately of this weight.

The dyeing composition according to the invention can also include various adjuvants conventionally used in hair dyeing compositions, such as anionic, cationic, nonionic, amphoteric or zwitterionic surface-active agents or their mixtures, anionic, cationic, nonionic, amphoteric or zwitterionic polymers or their mixtures, inorganic or organic thickening agents, anti-oxidizing agents, penetrating agents, sequestering agents, fragrances, buffers, dispersing agents, conditioning agents, such as, for example, silicones, film-forming agents, preservatives or opacifying agents.

Of course, a person skilled in the art will take care to choose this or these optional additional compound or compounds so that the advantageous properties intrinsically attached to the oxidation dyeing composition in accordance with the invention are not, or not substantially, detrimentally affected by the envisaged addition or additions.

The dyeing composition according to the invention can be provided in various forms, such as in the form of liquids, creams or gels, or in any other form appropriate for carrying out dyeing of keratinous fibres and in particular of human hair.

Another subject-matter of the invention is a method for dyeing keratinous fibres and in particular human keratinous fibres, such as hair, employing the dyeing composition as defined above.

According to this method, at least one dyeing composition as defined above is applied to the fibres for a time sufficient to develop the desired coloration, either with air or using an oxidizing agent.

According to a first embodiment of the method of the invention, the coloration of the fibres can be carried out without addition of an oxidizing agent, with contact only with atmospheric oxygen. In this case, the dyeing composition can then optionally comprise oxidation catalysts, in order to accelerate the oxidation process.

Mention may more particularly be made, as oxidation catalyst, of metal salts, such as manganese, cobalt, copper, iron, silver and zinc salts.

Such compounds are, for example, manganese diacetate tetrahydrate, manganese dichloride and its hydrates, manganese dihydrogencarbonate, manganese acetylacetonate, manganese triacetate and its hydrates, manganese trichloride, zinc dichloride, zinc diacetate dihydrate, zinc carbonate, zinc dinitrate, zinc sulphate, iron dichloride, iron sulphate, iron diacetate, cobalt diacetate tetrahydrate, cobalt carbonate, cobalt dichloride, cobalt dinitrate, cobalt sulphate heptahydrate, cupric chloride or ammoniacal silver nitrate.

Manganese salts are particularly preferred.

When they are used, these metal salts are generally employed in proportions varying between 0.001 and 4% by weight of metal equivalent with respect to the total weight of the dyeing composition and preferably between 0.005 and 2% by weight of metal equivalent with respect to the total weight of the dyeing composition.

According to a second embodiment of the method of the invention, at least one dyeing composition as defined above is applied to the fibres, the colour being developed at acidic, neutral or alkaline pH using an oxidizing agent which is added only at the time of use to the dyeing composition or which is present in an oxidizing composition applied simultaneously or sequentially in a separate fashion.

According to this second embodiment of the dyeing method of the invention, the dyeing composition described above is preferably mixed, at the time of use, with an oxidizing composition comprising, in a medium appropriate for dyeing, at least one oxidizing agent present in an amount sufficient to develop a coloration. The mixture obtained is subsequently applied to the keratinous fibres and left in contact for 3 to 50 minutes approximately, preferably 5 to 30 minutes approximately, after which the hair is rinsed, washed with shampoo, rinsed again and dried.

The oxidizing agent present in the oxidizing composition as defined above can be chosen from oxidizing agents conventionally used for the oxidation dyeing of keratinous fibres, among which may be mentioned hydrogen peroxide, urea hydrogen peroxide, alkali metal bromates, or persalts, such as perborates and persulphates. Hydrogen peroxide is particularly preferred.

The pH of the oxidizing composition including the oxidizing agent as defined above is such that, after mixing with the dyeing composition, the pH of the resulting composition applied to the keratinous fibres preferably varies between 3 and 12 approximately and more preferably still between 5 and 11. It is adjusted to the desired value by means of acidifying or basifying agents commonly used in dyeing keratinous fibres and as defined above.

The oxidizing composition as defined above can also include various adjuvants conventionally used in hair dyeing compositions and as defined above.

The composition which is finally applied to the keratinous fibres can be provided in various forms, such as in the form of liquids, creams or gels, or in any other form appropriate for carrying out dyeing of keratinous fibres, in particular of human hair.

Another subject-matter of the invention is a multi-compartment dyeing device or a dyeing "kit" or any other multi-compartment packaging system, a first compartment of which includes the dyeing composition as defined above and a second compartment of which includes the oxidizing composition as defined above. These devices can be equipped with a means which makes it possible to deliver the desired mixture onto the hair, such as the devices disclosed in Patent FR-2,586,913 on behalf of the Applicant Company.

The following examples are intended to illustrate the invention without limiting the scope thereof.

EXAMPLES

Preparation Example 1

Synthesis of 3,4-diamino-5-methyl-1H-pyrazole dihydrochloride:

a) Preparation of 3-acetamido-5-methyl-1H-pyrazole 50.4 g (0.6 mol) of sodium bicarbonate were added in small amounts at room temperature to a solution of 19.4 g (0.2 mol) of 3-amino-5-methyl-1H-pyrazole in 200 cm$^3$ of water. 37.8 cm$^3$ (0.4 mol) of acetic anhydride were added dropwise to this solution and then the mixture was heated at reflux for 2 hours. The solution was subsequently brought back to room temperature, a white solid crystallized and was pulled dry on sintered glass and then washed with 100 cm$^3$ of water. After drying under vacuum at 40° C., 16.6 g of the expected product were obtained in the form of pearlescent-white crystals, the melting point of which was between 210° C. and 212° C.

b) Preparation of 3-acetamido-5-methyl-4-nitro-1H-pyrazole 13.9 g (0.1 mol) of 3-acetamido-5-methyl-1H-pyrazole obtained in the preceding stage were added in small amounts to 140 cm$^3$ of 98% sulphuric acid at 5° C. 6.2 cm$^3$ of fuming nitric acid (d:1.52) were added dropwise to this solution, at 0° C., while maintaining the temperature between 0 and 5° C. during the introduction and for 30 minutes afterwards. The solution was subsequently poured onto 350 g of ice. A pale-yellow solid crystallized and was pulled dry on sintered glass and then washed with 100 cm$^3$ of water. After drying under vacuum at 40° C., 10 g of the expected product were obtained in the form of pale-yellow crystals, the melting point of which was between 240 and 242° C.

c) Preparation of 3-acetamido-4-amino-5-methyl-1H-pyrazole 2 g of 5% by weight palladium-on-charcoal comprising 50% water were added to a solution of 9.2 g (0.05 mol) of the product obtained in the preceding stage in a mixture of 400 cm³ of THF and 400 cm³ of ethanol. The suspension was placed in a hydrogenator under a pressure of 20 bar of hydrogen at 30° C. for 4 hours with vigorous agitation.

The contents of the hydrogenator were subsequently removed and filtered on sintered glass. This solution was concentrated under vacuum. A thick oil was obtained which crystallized by addition of 50 cm³ of isopropyl ether. A beige solid was pulled dry on sintered glass and then washed with 50 cm³ of isopropyl ether. After drying under vacuum at 40° C., 5 g of the expected product were obtained in the form of beige crystals, the melting point of which was between 270 and 272° C.

d) Preparation of 3-4-diamino-5-methyl-1H-pyrazole dihydrochloride

A solution of 4.6 g (0.03 mol) of the product obtained in the preceding stage in 100 cm³ of approximately 6N hydrochloric acid was heated [lacuna] reflux for 3 hours. This solution was concentrated under vacuum. A white solid crystallized and was pulled dry on sintered glass and then washed with 50 cm³ or isopropyl ether. A white solid was obtained which was recrystallized from a mixture of 25 cm³ of 3.5M ethanolic hydrochloric acid and 6 cm³ of water. After drying under vacuum at room temperature, 4 g of the expected product were obtained in the form of white crystals, the melting point of which was between 220 and 222° C. The elemental analysis for $C_4H_8N_4 \cdot 2HCl$ was:

|  | % | | | |
|---|---|---|---|---|
|  | C | H | N | Cl |
| Calculated | 25.96 | 5.45 | 30.28 | 38.32 |
| Found | 25.91 | 5.55 | 30.32 | 38.05 |

Preparation Example 2

Synthesis of 3-4-diamino-1,5-dimethylpyrazole dihydrochloride:

a) Preparation of 3-benzoylamino-5-methyl-1H-pyrazole 103 g (1 mol) of calcium carbonate were added with stirring to a solution of 50 g (0.5 mol) of 3-amino-5-methyl-1H-pyrazole in 100 cm³ of dioxane. 73 cm³ (0.6 mol) of benzoyl chloride were added dropwise to this solution at 65° C. The temperature was brought to 80° C. and maintained for 1 hour. The solution was subsequently brought back to 10° C. A beige solid formed during the reaction was pulled dry on sintered glass and was then taken up again with stirring in 400 cm³ of methanol. The solution was filtered and the filtrate was concentrated under vacuum. A beige solid crystallized and was pulled dry on sintered glass and then washed with 50 cm³ of isopropyl ether. After drying under vacuum at 40° C., 25 g of the expected product were obtained in the form of beige crystals, the melting point of which was between 218 and 220° C.

b) Preparation of 3-benzoylamino-1,5-dimethylpyrazole 62 cm³ (1 mol) of iodomethane were added to a solution of 20 g (0.1 mol) of the product obtained in the preceding stage and 27.6 g (0.2 mol) of potassium carbonate in 1 liter of THF at 50° C. and then the mixture was heated at reflux for 6 hours. The solution was brought back to room temperature. The potassium iodide formed was filtered and washed with 100 cm³ of THF. The filtrate was concentrated under vacuum. A thick yellow oil was obtained, which oil was crystallized by addition of 200 cm³ of isopropyl ether. A white solid was pulled dry on sintered glass and then washed with 50 cm³ of isopropyl ether. After drying under vacuum at 40° C., 18.7 g of the expected product and its isomer were obtained, which products were separated by column chromatography. After treatment and drying under vacuum at 40° C., 9 g of the expected product were obtained in the form of white crystals, the melting point of which was between 140 and 142° C.

c) Preparation of 3-(meta-nitrobenzoylamino)-1,5-dimethyl-4-nitropyrazole 9 g (0.04 mol) of the product obtained in the preceding stage were added in small amounts to 50 cm³ of 98% sulphuric acid at 5° C. 3.3 cm³ (0.08 mol) of fuming nitric acid (d:1.52) were added to this solution, at 0° C., while maintaining the temperature between 0 and 5° C. during the introduction and for 30 minutes afterwards. The solution was poured onto 300 g of ice. A yellow solid crystallized and was pulled dry on sintered glass and then washed with 100 cm³ of water. After drying under vacuum at 40° C., 10 g of the expected product were obtained in the form of yellow crystals, the melting point of which was between 170 and 172° C.

d) Preparation of 3-amino-1,5-dimethyl-4-nitropyrazole

A solution of 9.7 g (0.03 mol) of the product obtained in the preceding stage in 100 cm³ of approximately 6N hydrochloric acid was heated at reflux for 3 hours. This solution was brought back to room temperature and then chilled, the nitrobenzoic acid was filtered off and the filtrate was concentrated under vacuum. A yellow solid crystallized and was pulled dry on sintered glass and then washed with 20 cm³ of absolute ethanol. After drying under vacuum at 40° C. 4.2 g of the expected product were obtained in the form of yellow crystals, the melting point of which was between 210 and 212° C.

e) Preparation of 3-4-diamino-1,5-dimethylpyrazole dihydrochloride 0.5 g of 5% by weight palladium-on-charcoal comprising 50% water was added to a solution of 3.1 g (0.02 mol) of 3-amino-1,5-dimethyl-4-nitropyrazole obtained in the preceding stage in 150 [lacuna] of methanol. The suspension was placed in a hydrogenator under a pressure of 20 bar of hydrogen at 70° C. for 2 hours with vigorous agitation. The contents of the hydrogenator were removed and filtered on sintered glass. The filtrate was subsequently poured into 75 cm³ of a 3.5M ethanolic hydrochloric acid solution. This solution was concentrated under vacuum. A thick oil was obtained which crystallized by addition of 50 cm³ of isopropyl ether. A white solid was obtained which was recrystallized from a mixture of 25 cm³ of absolute ethanol at 80° C. and 5 cm³ of approximately 6N hydrochloric acid. After drying under vacuum at room temperature, 2.8 g of the expected product were obtained in the form of white crystals, the melting point of which was between 240 and 242° C. The elemental analysis for $C_5H_{10}N_4 \cdot 2HCl$ was:

|  | % | | | |
|---|---|---|---|---|
|  | C | H | N | Cl |
| Calculated | 30.17 | 6.08 | 28.14 | 35.62 |
| Found | 30.13 | 6.07 | 28.06 | 35.58 |

Dyeing Examples

Dyeing Examples 1 to 3 in Alkaline Medium

Two dyeing compositions 1 and 2 in accordance with the invention and a dyeing composition 3 according to the state of the art, in particular according to Patent Application EP-A-375,977, were prepared (contents in grams):

| COMPOSITION | 1 | 2 | 3 |
|---|---|---|---|
| 3,4-Diamino-1,5-dimethylpyrazole dihydrochloride (invention) | 0.597 | 0.597 | — |
| 3,4-Diamino-1-methylpyrazole (state of the art) | — | — | 0.555 |
| 1-Methyl-2-hydroxy-4-[β-(hydroxyethyl)amino]benzene (coupler) | 0.501 | — | 0.501 |
| 1-β-Hydroxyethyloxy-2,4-diaminobenzene dihydrochloride (coupler) | — | 0.723 | — |
| Common dyeing vehicle | (*) | (*) | (*) |
| Demineralized water, q.s. for | 100 g | 100 g | 100 g |

(*) common dyeing vehicle:

- Olyeyl alcohol polyglycerolated with 2 mol of glycerol — 4.0 g
- Olyel alcohol polyglycerolated with 4 mol of glycerol, containing 78% of active materials (A.M.) — 5.69 g A.M.
- Oleic acid — 3.0 g
- Oleylamine containing 2 mol of ethylene oxide, sold under the trade name Ethomeen 012 by the company Akzo — 7.0 g
- Diethylaminopropyl laurylamino-succinamate, sodium salt, containing 55% of A.M. — 3.0 g A.M.
- Oleyl alcohol — 5.0 g
- Oleic acid diethanolamide — 12.0 g
- Propylene glycol — 3.5 g
- Ethyl alcohol — 7.0 g
- Dipropylene glycol — 0.5 g
- Propylene glycol monomethyl ether — 9.0 g
- Sodium metabisulphite as an aqueous solution containing 35% of A.M. — 0.455 g A.M.
- Ammonium acetate — 0.8 g
- Anti-oxidizing agent, sequestering agent — q.s.
- Fragrance, preservative — q.s.
- Aqueous ammonia solution containing 20% of NH$_3$ — 10 g At the time of use, each dyeing composition 1, 2 or 3 was mixed with an equal amount by weight of an oxidizing composition composed of a 20 volumes aqueous hydrogen peroxide solution (6% by weight).

Each resulting composition was applied for 30 minutes to locks of natural grey hair containing 90% of white hairs, which hair may or may not have been permanently waved, in a proportion of 28 g per 3 g of hair. The locks of hair were subsequently rinsed, washed with a standard shampoo and then dried.

The colour of the locks was evaluated in the Munsell system by means of a CM 2002 Minolta calorimeter.

According to the Munsell notation, a colour is defined by the expression HV/C, in which the three parameters respectively denote the tint or Hue (H), the intensity or Value (V) and the purity or Chromaticity (C); the oblique stroke of this expression is simply a convention and does not indicate a ratio.

Colour of the locks of natural hair before dyeing; 3.8Y 5.4/1.5

Colour of the locks of permanent-waved hair before dyeing: 4.0Y 5.6/1.4.

The dyeing results are given in the following Table I:

TABLE I

| EXAMPLE | PH OF THE MIXTURE | Coloration obtained on natural hair | Coloration obtained on permanent-waved hair |
|---|---|---|---|
| 1 (invention) | 9.9 | 0.8 YR 5.0/3.2 coppery iridescent beige highlight | 7.6 R 4.3/4.6 coppery iridescent highlight |
| 2 (invention) | 9.9 | 9.1 RP 3.7/1.8 ash-violet highlight | 6.2 RP 2.8/1.8 purple highlight |
| 3 (prior art) | 9.8 | 2.3 YR 5.1/2.8 iridescent golden beige highlight | 0.9 YR 4.8/3.6 iridescent coppery highlight |

1. Test of Resistance to Light

A test of resistance to light (Xenotest) is carried out on locks of natural or permanent-waved hair dyed according to the dyeing method described above.

To do this, the locks of dyed hair were attached to a support (cardboard or plastic). These supports were placed on sample holders which were rotated about a Xenon lamp for a time of 40 hours under a relative humidity of 25±5% and at a temperature of 42.5±2.5° C.

The colour of the locks was evaluated in the Munsell system, before and after the test of resistance to light, by means of a CM 2002 Minolta calorimeter.

The difference in colour of each lock before and after the test of resistance to light reflects the deterioration in the coloration due to the action of light and was calculated by applying the Nickerson formula:

$$\Delta E = 0.4 Co \Delta H + 6 \Delta V + 3 \Delta C,$$

as described, for example, in "Couleur, Industrie et Technique" [Colour, Industry and Technology], pages 14–17, Vol. No. 5, 1978.

In this formula, ΔE represents the difference in colour between two locks, ΔH, ΔV and ΔC represent the variation in absolute value of the parameters H, V and C, and Co represents the purity of the lock with respect to which it is desired to evaluate the difference in colour (purity of the lock before the test).

Colour of the locks of natural hair before dyeing: 3.4Y 6.1/1.7.

Colour of the locks of permanent-waved hair before dyeing: 3.8Y 6.0/1.6.

The results of all the tests are given in Table II below:

TABLE II

| EXAMPLE | Shade obtained before light test on natural hair | Shade obtained before light test on permanent-waved hair | Shade obtained after light test on natural hair | Shade obtained after light test on permanent-waved hair | % of deterioration in the coloration on natural hair ΔE | % of deterioration in the coloration on permanent-waved hair ΔE |
|---|---|---|---|---|---|---|
| 1 (invention) | 1.9YR 5.2/3.0 | 9.9R 4.9/3.6 | 4.0YR 5.4/2.7 | 1.5YR 5.0/3.2 | 27.0 | 19.1 |
| 3 (comparison) | 2.7YR 5.5/3.0 | 2.5YR 5.0/3.2 | 6.5YR 5.8/2.2 | 5.0YR 5.4/2.7 | 59.3 | 39.4 |

It is found that the coloration obtained with the dyeing composition of Example 1 according to the invention (including 3,4-diamino-1,5-dimethylpyrazole dihydrochloride) resists the action of light much better than the coloration obtained with the dyeing composition of Example 3, which does not form part of the invention as it contains 3,4-diamino-1-methylpyrazole, a compound which does not correspond to the formula (I) defined above and which corresponds to a compound of the prior art as disclosed in EP-A-375,977.

2. Absorption of the Coloration on Locks

The difference between the colour of the locks before and after dyeing was calculated by applying the Nickerson formula:

$$SE = 0.4 C_0 \Delta H + 6 \Delta V + 3 \Delta C$$

In this formula, SE represents the difference in colour between two locks, ΔH, ΔV and ΔC represent the variation in absolute value of the parameters H, V and C, and $C_0$ represents the purity of the lock with respect to which it is desired to evaluate the difference in colour. SE thus reflects the dye absorption obtained, which increases as the value of SE increases.

Colour of the locks of natural hair before dyeing: 3.8Y 5.4/1.5

Colour of the locks of permanent-waved hair before dyeing: 4.0Y 5.6/1.4.

The colour of the locks was evaluated in the Munsell system, by means of a CM 2002 Minolta calorimeter.

The results are given in Table III below:

TABLE III

| EXAMPLE | Shade obtained after dyeing on natural hair | Shade obtained after dyeing on permanent-waved hair | SE: Absorption of dye on natural hair | SE: Absorption of dye on permanent-waved hair |
|---|---|---|---|---|
| 1 (invention) | 0.8 YR 5.0/3.2 coppery iridescent beige highlight | 7.6 R 4.3/4.6 coppery iridescent highlight | 15.3 | 26.6 |
| 3 (comparative) | 2.3 YR 5.1/2.8 iridescent golden beige highlight | 0.9 YR 4.8/3.6 iridescent coppery highlight | 12.3 | 18.7 |
| | | | 12.3 | 18.7 |

It is found that the dyeing composition of Example 1 according to the invention (including 3,4-diamino-1,5-dimethylpyrazole dihydrochloride) results in more intense colorations than the dyeing composition of Example 3, which does not form part of the invention as it contains 3,4-diamino-1-methylpyrazole, a compound which does not correspond to the formula (I) as defined above and which corresponds to a compound of the prior art as disclosed in EP-A-375,977.

Dyeing Examples 4 and 5 in Acidic Medium

The following dyeing compositions in accordance with the invention were prepared (contents in grams):

| COMPOSITION | 4 | 5 |
|---|---|---|
| 3,4-Diamino-1,5-dimethylpyrazole dihydrochloride (invention) | 0.597 | 0.597 |
| 1-Methyl-2-hydroxy-4-[β-(hydroxyethyl)amino]benzene (coupler) | 0.501 | — |
| 1-β-Hydroxyethyloxy-2,4-diaminobenzene dihydrochloride (coupler) | | 0.723 |
| Common dyeing vehicle | (*) | (*) |
| Demineralized water, q.s. for | 100 g | 100 g |

| (*) common dyeing vehicle: | |
|---|---|
| - Oleyl alcohol polyglycerolated with 2 mol of glycerol | 4.0 g |
| - Oleyl alcohol polyglycerolated with 4 mol of glycerol containing 78% of active materials (A.M.) | 5.69 g A.M. |
| - Oleic acid | 3.0 g |
| - Oleylamine containing 2 mol of ethylene oxide, sold under the trade name Ethomeen 012 by the company Akzo | 7.0 g |
| - Diethylaminopropyl laurylamino-succinamate, sodium salt, containing 55% of A.M. | 3.0 g A.M. |
| - Oleyl alcohol | 5.0 g |
| - Oleic acid diethanolamide | 12.0 g |
| - Propylene glycol | 3.5 g |
| - Ethyl alcohol | 7.0 g |
| - Dipropylene glycol | 0.5 g |
| - Propylene glycol monomethyl ether | 9.0 g |
| - Sodium metabisulphite as an aqueous solution containing 35% of A.M | 0.455 g A.M. |
| - Ammonium acetate | 0.8 g |
| - Anti-oxidizing agent, sequestering agent | q.s. |
| - Fragrance, preservative | q.s. |
| - Monoethanolamine, q.s. for | pH 9.8 |

At the time of use, each dyeing composition 4 and 5 was mixed with an equal amount by weight of an oxidizing composition composed of a 20 volumes aqueous hydrogen peroxide solution (6% by weight), the pH of which had been adjusted between 1 and 1.5 with 2.5 g of orthophosphoric acid per 100 g of aqueous hydrogen peroxide solution.

Each resulting composition was applied for 30 minutes to locks of natural grey hair containing 90% of white hairs, which hair may or may not have been permanently waved, in a proportion of 28 g per 3 g of hair. The locks of hair were subsequently rinsed, washed with a standard shampoo and then dried.

The colour of the locks was evaluated in the Munsell system by means of a CM 2002 Minolta calorimeter.

Colour of the locks of natural hair before dyeing: 3.8Y 5.4/1.5

Colour of the locks of permanent-waved hair before dyeing: 4.0Y 5.6/1.4.

The dyeing results are given in the following Table IV:

benzyl radical; or a benzyl radical substituted by a halogen atom or by a $C_1$–$C_4$ alkyl, $C_1$–$C_4$ alkoxy, methylenedioxy, hydroxyl, $C_1$–$C_4$ hydroxyalkyl, amino or $C_1$–$C_4$ alkylamino radical;

wherein at most one of the radicals $R_2$ to $R_5$ can denote a radical

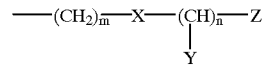

wherein m and n, which are identical or different, are integers from 1 to 3 inclusive, X represents an oxygen atom or an NH group, Y represents a hydrogen atom or a methyl radical, and Z represents a methyl radical or an OR or NRR' group wherein R and R', which can be identical or different, denote a hydrogen atom, a methyl radical or an ethyl radical;

TABLE IV

| Example | pH of the mixture | Coloration obtained on natural hair | Coloration obtained on permanent-waved hair | Absorption of the coloration on natural hair (SE) | Absorption of the coloration on permanent-waved hair (SE) |
|---|---|---|---|---|---|
| 1 | 9.9 | 0.8YR 5.0/3.2 coppery iridescent beige highlight | 7.6R 4.3/4.6 coppery iridescent highlight | 15.3 | 26.6 |
| 4 | 6.8 | 8.5R 4.4/3.5 broadly golden iridescent highlight | 6.0R 3.9/4.3 red iridescent highlight | 21.2 | 28.9 |
| 2 | 9.9 | 9.1RP 3.7/1.8 ash-violet highlight | 6.2RP 2.8/1.8 purple highlight | 25.9 | 33.6 |
| 5 | 6.8 | 8.2RP 3.2/1.6 ash-violet highlight | 7.3RP 2.6/1.8 purple highlight | 28.9 | 34.2 |

It is found that the dyeing compositions of Examples 4 and 5 according to the invention (including 3,4-diamino-1,5-dimethylpyrazole dihydrochloride), applied to locks in acidic medium, result in more intense colorations than respectively the dyeing compositions of Examples 1 and 2, applied to locks in alkaline medium and including the same oxidation base (3,4-diamino-1,5-dimethylpyrazole dihydrochloride) and the same coupler (1-methyl-2-hydroxy-4-[β-(hydroxyethyl)amino]benzene or 1-β-hydroxyethyloxy-2,4-diaminobenzene dihydrochloride).

We claim:

1. A 5-substituted 3,4-diaminopyrazole compound of formula (I) or an acid addition salt thereof:

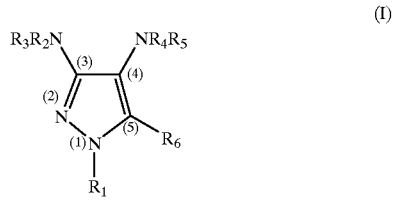

wherein:

$R_1$, $R_2$, $R_3$, $R_4$ and $R_5$, each represent a hydrogen atom; a linear or branched $C_1$–$C_6$ alkyl radical; a $C_2$–$C_4$ hydroxyalkyl radical; a $C_2$–$C_4$ aminoalkyl radical; a phenyl radical; a phenyl radical substituted by a halogen atom or a $C_1$–$C_4$ alkyl, $C_1$–$C_4$ alkoxy, nitro, trifluoromethyl, amino or $C_1$–$C_4$ alkylamino radical; a with the proviso that, when $R_2$ represents a hydrogen atom, then $R_3$ can represent an amino or $C_1$–$C_4$ alkylamino radical;

$R_6$ represents a linear or branched $C_1$–$C_8$ alkyl radical; a $C_1$–$C_4$ hydroxyalkyl radical; a $C_1$–$C_4$ aminoalkyl radical; a phenyl radical; a phenyl radical substituted by a halogen atom or by a $C_1$–$C_4$ alkyl, $C_1$–$C_4$ alkoxy, nitro, trifluoromethyl, amino or $C_1$–$C_4$ alkylamino radical; a benzyl radical; a benzyl radical substituted by a halogen atom or by a $C_1$–$C_4$ alkyl, $C_1$–$C_4$ alkoxy, nitro, trifluoromethyl, amino or $C_1$–$C_4$ alkylamino radical; a heterocycle which is thiophene, furan, or pyridine; or a —$(CH_2)_p$—O—O—$(CH_2)_1$—OR" radical, in which p and q, which are identical or different, are integers from 1 to 3 inclusive and R" represents a hydrogen atom or a methyl radical;

wherein in formula (I):

(i) at least one of $R_4$ and $R_5$ represents a hydrogen atom, (ii) when $R_2$ or $R_4$ represents a substituted or unsubstituted phenyl radical, a benzyl radical, or a radical

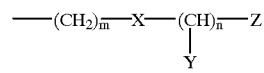

then $R_3$ or $R_5$ cannot represent any of these three radicals, (iii) $R_1$ can also represent a heterocyclic residue of 2-, 3- or 4-pyridyl, 2- or 3-thienyl, or 2- or 3-furyl, optionally substituted by a methyl radical, and (iv) when $R_2, R_3, R_4$, and $R_5$ are all hydrogen, then $R_6$ cannot be methyl, methoxy, or phenyl.

2. A compound of formula (I) according to claim 1, wherein said compound is:
3,4-diamino-5-ethylpyrazole;
3,4-diamino-5-isopropylpyrazole;
3,4-diamino-5-tert-butylpyrazole;
3,4-diamino-5-(4'-methoxyphenyl)pyrazole;
3,4-diamino-5-(3'-methoxyphenyl)pyrazole;
3,4-diamino-5-(2'-methoxyphenyl)pyrazole;
3,4-diamino-5-(4'-methylphenyl)pyrazole;
3,4-diamino-5-(3'-methylphenyl)pyrazole;
3,4-diamino-5-(2'-chlorophenyl)pyrazole;
3,4-diamino-5-(4'-chlorophenyl)pyrazole;
3,4-diamino-5-(3'-trifluoromethylphenyl)pyrazole;
3,4-diamino-1,5-dimethylpyrazole;
3,4-diamino-5-ethyl-1-methylpyrazole;
3,4-diamino-1-methyl-5-tert-butylpyrazole;
3,4-diamino-1-methyl-5-phenylpyrazole;
3,4-diamino-1-methyl-5-methoxypyrazole;
3,4-diamino-1-methyl-5-(4'-methoxyphenyl)pyrazole;
3,4-diamino-1-methyl-5-(3'-methoxyphenyl)pyrazole;
3,4-diamino-1-methyl-5-(2'-methoxyphenyl)pyrazole;
3,4-diamino-1-methyl-5-(4'-methylphenyl)pyrazole;
3,4-diamino-1-methyl-5-(3'-methylphenyl)pyrazole;
3,4-diamino-5-(2'-chlorophenyl)-1-methylpyrazole;
3,4-diamino-5-(4'-chlorophenyl)-1-methylpyrazole;
3,4-diamino-5-(3'-trifluoromethylphenyl)-1-methylpyrazole;
3,4-diamino-1-ethyl-5-methylpyrazole;
3,4-diamino-1,5-diethylpyrazole;
3,4-diamino-1-ethyl-5-tert-butylpyrazole;
3,4-diamino-1-ethyl-5-phenylpyrazole;
3,4-diamino-1-ethyl-5-methoxypyrazole;
3,4-diamino-1-ethyl-5-(4'-methoxyphenyl)pyrazole;
3,4-diamino-1-ethyl-5-(3'-methoxyphenyl)pyrazole;
3,4-diamino-1-ethyl-5-(2'-methoxyphenyl)pyrazole;
3,4-diamino-1-ethyl-5-(4'-methylphenyl)pyrazole;
3,4-diamino-1-ethyl-5-(3'-methylphenyl)pyrazole;
3,4-diamino-5-(2'-chlorophenyl)-1-ethylpyrazole;
3,4-diamino-5-(4'-chlorophenyl)-1-ethylpyrazole;
3,4-diamino-1-ethyl-5-(3'-trifluoromethylphenyl)pyrazole;
3,4-diamino-1-isopropyl-5-methylpyrazole;
3,4-diamino-5-ethyl-1-isopropylpyrazole;
3,4-diamino-1-isopropyl-5-tert-butylpyrazole;
3,4-diamino-1-isopropyl-5-phenylpyrazole;
3,4-diamino-1-isopropyl-5-methoxypyrazole;
3,4-diamino-1-isopropyl-5-(4'-methoxyphenyl)pyrazole;
3,4-diamino-1-isopropyl-5-(3'-methoxyphenyl)pyrazole;
3,4-diamino-1-isopropyl-5-(2'-methoxyphenyl)pyrazole;
3,4-diamino-1-isopropyl-5-(4'-methylphenyl)pyrazole;
3,4-diamino-1-isopropyl-5-(3'-methylphenyl)pyrazole;
3,4-diamino-5-(2'-chlorophenyl)-1-isopropylpyrazole;
3,4-diamino-5-(4'-chlorophenyl)-1-isopropylpyrazole;
3,4-diamino-1-isopropyl-5-(3'-trifluoromethylphenyl)pyrazole;
3,4-diamino-5-methyl-1-propylpyrazole;
3,4-diamino-5-ethyl-1-propylpyrazole;
3,4-diamino-1-propyl-5-tert-butylpyrazole;
3,4-diamino-5-phenyl-1-propylpyrazole;
3,4-diamino-5-methoxy-1-propylpyrazole;
3,4-diamino-5-(4'-methoxyphenyl)-1-propylpyrazole;
3,4-diamino-5-(3'-methoxyphenyl)-1-propylpyrazole;
3,4-diamino-5-(2'-methoxyphenyl)-1-propylpyrazole;
3,4-diamino-5-(4'-methylphenyl)-1-propylpyrazole;
3,4-diamino-5-(3'-methylphenyl)-1-propylpyrazole;
3,4-diamino-5-(2'-chlorophenyl)-1-propylpyrazole;
3,4-diamino-5-(4'-chlorophenyl)-1-propylpyrazole;
3,4-diamino-1-propyl-5-(3'-trifluoromethylphenyl)pyrazole;
1-benzyl-3,4-diamino-5-methylpyrazole;
1-benzyl-3,4-diamino-5-ethylpyrazole;
1-benzyl-3,4-diamino-5-tert-butylpyrazole;
1-benzyl-3,4-diamino-5-phenylpyrazole;
1-benzyl-3,4-diamino-5-methoxypyrazole;
1-benzyl-3,4-diamino-5-(4'-methoxyphenyl)pyrazole;
1-benzyl-3,4-diamino-5-(3'-methoxyphenyl)pyrazole;
1-benzyl-3,4-diamino-5-(2'-methoxyphenyl)pyrazole;
1-benzyl-3,4-diamino-5-(4'-methylphenyl)pyrazole;
1-benzyl-3,4-diamino-5-(3'-methylphenyl)pyrazole;
1-benzyl-3,4-diamino-5-(2'-chlorophenyl)pyrazole;
1-benzyl-3,4-diamino-5-(4'-chlorophenyl)pyrazole;
1-benzyl-3,4-diamino-5-(3'-trifluoromethylphenyl)pyrazole;
1-[4'-chlorobenzyl]-3,4-diamino-5-methylpyrazole;
1-[4'-chlorobenzyl]-3,4-diamino-5-ethylpyrazole;
1-[4'-chlorobenzyl]-3,4-diamino-5-tert-butylpyrazole;
1-[4'-chlorobenzyl]-3,4-diamino-5-phenylpyrazole;
1-[4'-chlorobenzyl]-3,4-diamino-5-methoxypyrazole;
1-[4'-chlorobenzyl]-3,4-diamino-5-(4'-methoxyphenyl)pyrazole;
1-[4'-chlorobenzyl]-3,4-diamino-5-(3'-methoxyphenyl)pyrazole;
1-[4'-chlorobenzyl]-3,4-diamino-5-(2'-methoxyphenyl)pyrazole;
1-[4'-chlorobenzyl]-3,4-diamino-5-(4'-methylphenyl)pyrazole;
1-[4'-chlorobenzyl]-3,4-diamino-5-(3'-methylphenyl)pyrazole;
1-[4'-chlorobenzyl]-3,4-diamino-5-(2'-chlorophenyl)pyrazole;
1-[4'-chlorobenzyl]-3,4-diamino-5-(4'-chlorophenyl)pyrazole;
1-[4'-chlorobenzyl]-3,4-diamino-5-(3'-trifluoromethylphenyl)pyrazole;
3,4-diamino-5-hydroxymethyl-1-methylpyrazole;
3,4-diamino-5-hydroxymethyl-1-ethylpyrazole;
3,4-diamino-5-hydroxymethyl-1-isopropylpyrazole;
3,4-diamino-5-hydroxymethyl-1-propylpyrazole;
1-benzyl-3,4-diamino-5-hydroxymethylpyrazole;
1-[4'-chlorobenzyl]-3,4-diamino-5-hydroxymethylpyrazole;
5-aminomethyl-3,4-diamino-1-methylpyrazole;
5-aminomethyl-3,4-diamino-1-ethylpyrazole;
5-aminomethyl-3,4-diamino-1-isopropylpyrazole;
5-aminomethyl-3,4-diamino-1-propylpyrazole;
5-aminomethyl-1-benzyl-3,4-diaminopyrazole;
5-aminomethyl-1-[4'-chlorobenzyl]-3,4-diaminopyrazole;
3,4-diamino-5-hydroxymethylpyrazole;
3,4-diamino-5-[β-hydroxyethylamino]-1-methylpyrazole;
3,4-diamino-5-[β-hydroxyethylamino]-1-ethylpyrazole;
3,4-diamino-5-[β-hydroxyethylamino]-1-isopropylpyrazole;
3,4-diamino-5-[β-hydroxyethylamino]-1-propylpyrazole;
3,4-diamino-5-[β-hydroxyethylamino]pyrazole;
1-benzyl-3,4-diamino-5-[β-hydroxyethylamino]pyrazole; or
1-[4'-chlorobenzyl]-3,4-diamino-5-[β-hydroxyethylamino]pyrazole; or an acid addition salt thereof.

3. A compound of formula (I) according to claim 1, wherein the compound is:
3,4-diamino-5-ethylpyrazole;
3,4-diamino-5-isopropylpyrazole;
3,4-diamino-5-tert-butylpyrazole;
3,4-diamino-5-(4'-methoxyphenyl)pyrazole;
3,4-diamino-5-(3'-methoxyphenyl)pyrazole;
3,4-diamino-5-(2'-methoxyphenyl)pyrazole;

3,4-diamino-5-(4'-methylphenyl)pyrazole;
3,4-diamino-5-(3'-methylphenyl)pyrazole;
5-(2'-chlorophenyl)-3,4-diaminopyrazole;
5-(4'-chlorophenyl)-3,4-diaminopyrazole;
3,4-diamino-1,5-dimethylpyrazole;
3,4-diamino-5-ethyl-1-methylpyrazole;
3,4-diamino-5-isopropyl-1-methylpyrazole;
3,4-diamino-1-methyl-5-tert-butylpyrazole;
3,4-diamino-1-methyl-5-phenylpyrazole;
3,4-diamino-1-methyl-5-methoxypyrazole;
3,4-diamino-1-methyl-5-(4'-methoxyphenyl)pyrazole;
3,4-diamino-1-methyl-5-(3'-methoxyphenyl)pyrazole;
3,4-diamino-1-methyl-5-(2'-methoxyphenyl)pyrazole;
3,4-diamino-1-methyl-5-(4'-methylphenyl)pyrazole;
3,4-diamino-1-methyl-5-(3'-methylphenyl)pyrazole;
5-(2'-chlorophenyl)-3,4-diamino-1-methylpyrazole; or
5-(4'-chlorophenyl)-3,4-diamino-1-methylpyrazole; or an acid addition salt thereof.

4. A compound of formula (I) according to claim 1, wherein the compound is an acid addition salt, and the addition salt is a hydrochloride, hydrobromide, sulphate, tartrate, lactate, or acetate.

5. A method for the preparation of a compound of formula (I) according to claim 1 wherein $R_1$ represents a hydrogen atom, comprising:
(a) reacting a β-ketonitrile with hydrazine in an alcoholic solvent to obtain a 3-aminopyrazole,
(b) acetylating the 3-aminopyrazole at the 3 position to yield a 3-acetamidopyrazole,
(c) nitrating the 3-acetamidopyrazole at the 4 position;
(d) catalytically hydrogenating the product of step (c); and
(e) deacetylating the product of step (d) to yield the compound of formula (I) wherein $R_1$ represents a hydrogen atom.

6. A method for the preparation of a compound of formula (I) according to claim 1 wherein $R_1$ is other than a hydrogen atom, comprising:
(a) reacting a β-ketonitrile with hydrazine in an alcoholic solvent, to yield a 3-aminopyrazole;
(b) benzoylating the 3-aminoprazole at the 3 position, in the presence of benzoic acid chloride in an aprotic solvent and in the presence of an organic or inorganic base;
(c) reacting an aliphatic alkyl halide in an aprotic solvent, in order to obtain a mixture of a 5-benzoylaminopyrazole and of a 3-benzoylaminopyrazole;
(d) nitrating the 3-benzoylaminopyrazole obtained in step (c);
(e) debenzoylating the product of step (d) in the presence of hydrochloric acid and,
(f) catalytically hydrogenating the product of step (e), to provide a 3,4-diaminopyrazole of formula (I) in which $R_1$ is other than a hydrogen atom.

7. A composition for the oxidation dyeing of keratinous fibres, comprising, in a medium appropriate for dyeing, at least one 5-substituted 3,4-diaminopyrazole of formula (I) according to claim 1, or an acid addition salt thereof, as an oxidation base.

8. A composition according to claim 7, wherein said keratinous fibres are human hair.

9. A composition according to claim 7, wherein said at least one 5-substituted 3,4-diaminopyrazole of formula (I) is present in an amount ranging from 0.0005 to 12% by weight of the total weight of said composition.

10. A composition according to claim 9, wherein said at least one 5-substituted 3,4-diaminopyrazole of formula (I) is present in an amount ranging from 0.005 to 6% by weight of the total weight of said composition.

11. A composition according to claim 7, wherein the medium appropriate for dyeing comprises water or a mixture of water and an organic solvent, wherein the organic solvent is a lower $C_1$–$C_4$ alkanol, glycerol, glycol, glycol ether, aromatic alcohol, or a mixture thereof.

12. A composition according to claim 7, wherein said composition has a pH ranging from 3 to 12.

13. A composition according to claim 7, further comprising an additional oxidation base, other than said at least one 5-substituted 3,4-diaminopyrazole of formula (I), wherein the additional oxidation base is a para-phenylenediamine, bisphenylalkylenediamine, para-aminophenol, ortho-aminophenol or heterocyclic base.

14. A composition according to claim 13, wherein the additional oxidation base is present in an amount ranging from 0.0005 to 12% by weight of the total weight of said composition.

15. A composition according to claim 7, wherein the composition includes at least one of a coupler and a direct dye.

16. A composition according to claim 15, wherein the composition includes at least one coupler, and said at least one coupler is a meta-phenylenediamine, meta-aminophenol, meta-diphenol, or heterocyclic coupler, or an acid addition salt thereof.

17. A composition according to claim 15, wherein the composition includes at least one coupler present in an amount ranging from 0.0001 to 10% by weight of the total weight of the dyeing composition.

18. A composition according to claim 7, wherein the coupler is an acid addition salt, and the acid addition salt is a hydrochloride, hydrobromide, sulphate, tartrate, lactate, or acetate.

19. A method for dyeing keratinous fibres, comprising applying a dyeing composition as defined in claim 7 to human keratinous fibres for a time sufficient to develop the desired coloration, with air or with an oxidizing agent.

20. A method according to claim 19, wherein the human keratinous fibres are hair.

21. A method according to claim 19, wherein the coloration is developed by contact only with atmospheric oxygen.

22. A method according to claim 19, wherein the coloration is developed with contact only with atmospheric oxygen, in the presence of an oxidation catalyst.

23. A method according to claim 22, wherein the oxidation catalyst is a metal salt.

24. A method according to claim 19, further comprising developing said coloration at acidic, neutral, or alkaline pH in the presence of an oxidizing agent which is added to the dye composition only at the time or which is present in an oxidizing composition that is applied:
(i) separately from the dye composition at the same time that said dye composition is applied to said fibres, or
(ii) sequentially with the dye composition.

25. A method according to claim 24, wherein the oxidizing agent is hydrogen peroxide, urea hydrogen peroxide, an alkali metal bromate, or per salts.

26. A method according to claim 25, wherein the oxidizing agent is a per salt and is perborate or persulphate.

27. A multi-compartment device or multi-compartment dyeing kit, comprising a first compartment containing a dyeing composition as defined in claim 7 and a second compartment containing an oxidizing composition.

* * * * *

UNITED STATES PATENT AND TRADEMARK OFFICE
CERTIFICATE OF CORRECTION

PATENT NO. : 6,118,008

DATED: September 27, 2000

INVENTORS: Gèrard MALLE et al.

It is hereby certified that errors appear in the above-identified patent and that said Letters Patent is hereby corrected as shown below:

Claim 1, col. 20, line 50, change "$-(CH_2)_p-O-O-(CH_2)_1-OR''$" to

-- $-(CH_2)_p-O-(CH_2)_1-OR''$ --

Claim 2, col. 22, line 41, close up space in "-1 -propylpyrazole".

Signed and Sealed this

Twenty-fourth Day of April, 2001

Attest:

NICHOLAS P. GODICI

Attesting Officer

Acting Director of the United States Patent and Trademark Office